US011726074B2

(12) United States Patent
Martysevich et al.

(10) Patent No.: US 11,726,074 B2
(45) Date of Patent: Aug. 15, 2023

(54) METHOD, APPARATUS AND SYSTEM FOR ESTIMATION OF ROCK MECHANICAL PROPERTIES (71) Applicant: Halliburton Energy Services, Inc., Houston, TX (US)

(72) Inventors: Vladimir Nikolayevich Martysevich, Spring, TX (US); Jie Bai, Katy, TX (US); Ronald Glen Dusterhoft, Katy, TX (US); Harold Grayson Walters, Tomball, TX (US); Luis Matzar, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 674 days.

(21) Appl. No.: 16/757,258

(22) PCT Filed: Dec. 28, 2017

(86) PCT No.: PCT/US2017/068779
§ 371 (c)(1),
(2) Date: Apr. 17, 2020

(87) PCT Pub. No.: WO2019/132932
PCT Pub. Date: Jul. 4, 2019

(65) Prior Publication Data
US 2021/0190755 A1    Jun. 24, 2021

(51) Int. Cl.
*G01N 33/24* (2006.01)
*G01N 3/06* (2006.01)
(Continued)

(52) U.S. Cl.
CPC .............. *G01N 33/24* (2013.01); *G01N 3/06* (2013.01); *G01N 3/08* (2013.01); *G01N 3/02* (2013.01);
(Continued)

(58) Field of Classification Search
CPC ............ G01N 33/24; G01N 3/06; G01N 3/08; G01N 3/02; G01N 2203/0019; G01N 2203/0276
See application file for complete search history.

(56) References Cited

U.S. PATENT DOCUMENTS 4,236,413 A    12/1980  Schmid et al.
4,567,774 A    2/1986   Manahan et al.
(Continued)

FOREIGN PATENT DOCUMENTS

CN    205138899 U    4/2016
WO    2019132932 A1  7/2019

OTHER PUBLICATIONS

Lavrov, et al.; "Experimental and numerical study of the Kaiser effect in cyclic Brazilian tests with disk rotation" International Journal of Rock Mechanics and Mining Services, vol. 39, Issue 3; www.elsevier.com/locate/ijrmms; Mar. 18, 2002; 16 pgs.
(Continued)

*Primary Examiner* — Jonathan M Dunlap
(74) *Attorney, Agent, or Firm* — Michael Jenney; Parker Justiss, P.C.

(57) ABSTRACT

An apparatus for measuring mechanical properties of a rock formation. The apparatus includes force application fixtures configured to apply opposing compressive forces to a disc-shaped sample of a core plug specimen from the rock formation. Each of the force application fixtures include an applicant portion having an end cap. The end cap has a shaped surface that is configured to conform with a portion of a non-planar side of the disc-shaped sample such that substantially an entire volume of the disc-shaped sample experiences a compressive stress when the opposing compressive forces are applied to the portions of the non-planar side. A system and method for measuring mechanical properties of a rock formation are also disclosed.

19 Claims, 9 Drawing Sheets

(51) Int. Cl.
  *G01N 3/08* (2006.01)
  *G01N 3/02* (2006.01)
(52) U.S. Cl.
  CPC ............... *G01N 2203/0019* (2013.01); *G01N 2203/0276* (2013.01)

(56) References Cited

U.S. PATENT DOCUMENTS

| | | | |
|---|---|---|---|
| 5,482,122 | A | 1/1996 | Abass et al. |
| 6,952,969 | B2 | 10/2005 | O'Brien et al. |
| 7,650,795 | B2 | 1/2010 | Abousleiman et al. |
| 9,983,106 | B2 * | 5/2018 | Han ......................... G01N 3/08 |
| 2005/0066741 | A1 * | 3/2005 | O'Brien .................. G01N 3/08 73/821 |
| 2010/0224007 | A1 * | 9/2010 | Greszczuk ............... G01N 3/08 428/397 |
| 2016/0103047 | A1 | 4/2016 | Liu et al. |
| 2017/0299486 | A1 | 10/2017 | Han et al. |
| 2018/0088014 | A1 * | 3/2018 | Lai .......................... G01N 3/08 |

OTHER PUBLICATIONS

Markides, et al.; "Anisotropic discs loaded by parabolically distributed pressure"; Sciencedirect; Elsevier; www.sciencedirect.com; www.elsevier.com/locate/procedia; 21st European Conference on Fracture, ECF21; Jun. 20-24, 2016; 8 pgs.

Kourkoulis, et al.; "The Brazilian disc under parabolically varying load: Theoretical and experimental study of the displacement filed"; International Journal of Solids and Structures; Elsevier; www.elsevier.com/locate/ijsolstr; 2012; 14 pgs.

* cited by examiner

METHOD, APPARATUS AND SYSTEM FOR ESTIMATION OF ROCK MECHANICAL PROPERTIES

CROSS-REFERENCE TO RELATED APPLICATION

This application is the National Stage of, and therefore claims the benefit of, International Application No. PCT/US2017/068779 filed on Dec. 28, 2017, entitled "METHOD, APPARATUS AND SYSTEM FOR ESTIMATION OF ROCK MECHANICAL PROPERTIES," which was published in English under International Publication Number WO 2019/132932 on Jul. 4, 2019. The above application is commonly assigned with this National Stage application and is incorporated herein by reference in its entirety.

BACKGROUND

An on-going challenge in the oil and gas industry is to obtain reliable mechanical properties of formations having anisotropic material compositions. Such formations can have a plurality of millimeter-scale layers laminated together with each layer composed of different types of materials (e.g., clay, silica, or organic matter) and thus each having different mechanical properties. Consequently, different core plug specimens can have mechanical properties that can differ by several orders of magnitude. For example, different core plug specimens obtained from a whole core with a spacing of tens of centimeters between core plug specimens may have significant variations in mechanical properties, since different laminations of material can be present in the different plug specimens. Thus, classical rock mechanical property analysis obtained from such whole core operations cannot be reliably used for formations with anisotropic mechanical properties.

BRIEF DESCRIPTION

DETAILED DESCRIPTION

As part of the present invention, we recognized that prior testing methods often require the acquisition of multiple core specimens from formations with anisotropic material compositions to obtain just limited numbers of mechanical properties. In contrast, the approach of the present disclosure can obtain multiple different mechanical properties from a single core specimen. Since minimal specimen material is required (e.g., a single specimen), the effect of material composition heterogeneity in the formation of the measured mechanical properties can be minimized Consequently, the approach of the present disclosure provides a simple and economical way to more precisely obtain mechanical properties of any mechanically competent formation, including formations with anisotropic material compositions.

As further disclosed below, the apparatus, system and method of the disclosure facilitate compression testing of a single core plug specimen in multiple directions to detect rock formation anisotropic mechanical properties. In particular, multiple disc-shaped sample of the single core plug specimen can be sequentially compression tested at different angles, relative to an in situ force experienced by formation from which the core plug specimen was obtained, to evaluate the extent of heterogeneity in the mechanical properties.

In the drawings and descriptions to follow, like parts are typically marked throughout the specification and drawings with the same reference numerals, respectively. The drawn figures are not necessarily to scale. Certain features of this disclosure may be shown exaggerated in scale or in somewhat schematic form and some details of conventional elements may not be shown in the interest of clarity and conciseness. Specific embodiments are described in detail and are shown in the drawings, with the understanding that they serve as examples and that they do not limit the disclosure to only the illustrated embodiments. Moreover, it is fully recognized that the different teachings of the embodiments discussed, infra, may be employed separately or in any suitable combination to produce desired results.

Unless otherwise specified, any use of any form of the terms such as "press," "connect," "engage," "couple," "attach," or any other term describing an interaction between elements is not meant to limit the interaction to direct interaction between the elements but include indirect interaction between the elements described, as well. In the following discussion and in the claims, the terms "including" and "comprising" are used in an open-ended fashion, and thus should be interpreted to mean "including, but not limited to." Further, any references to "first," "second," etc. do not specify a preferred order of method or importance, unless otherwise specifically stated but are intended to designate separate elements. The various characteristics mentioned above, as well as other features and characteristics described in more detail below, will be readily apparent to those skilled in the art with the aid of this disclosure upon reading the following detailed description of the embodiments, and by referring to the accompanying drawings.

Figure 1A:
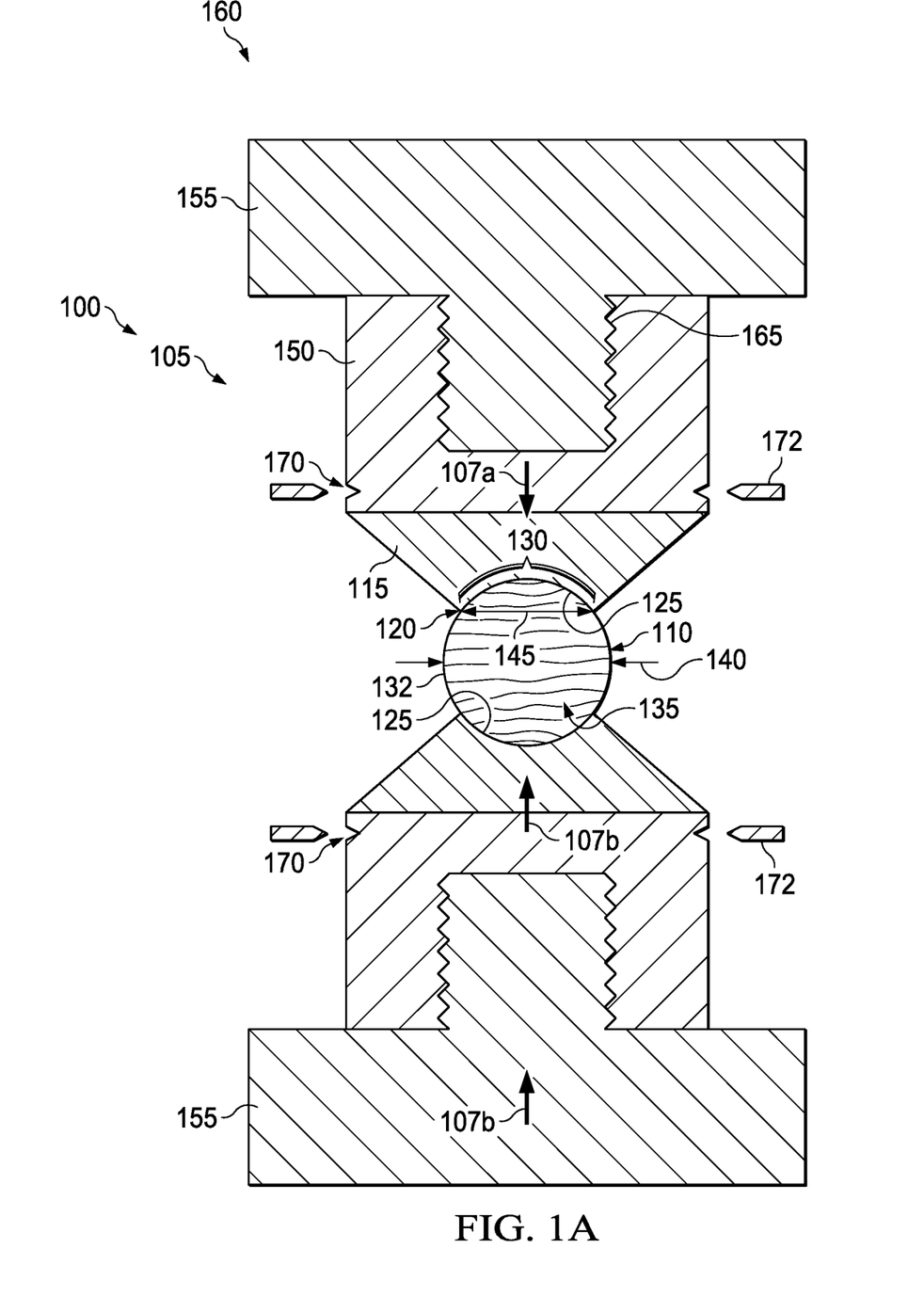
FIG. 1A presents a cross-sectional front view of an example apparatus embodiment of the disclosure.
Figure 1B:
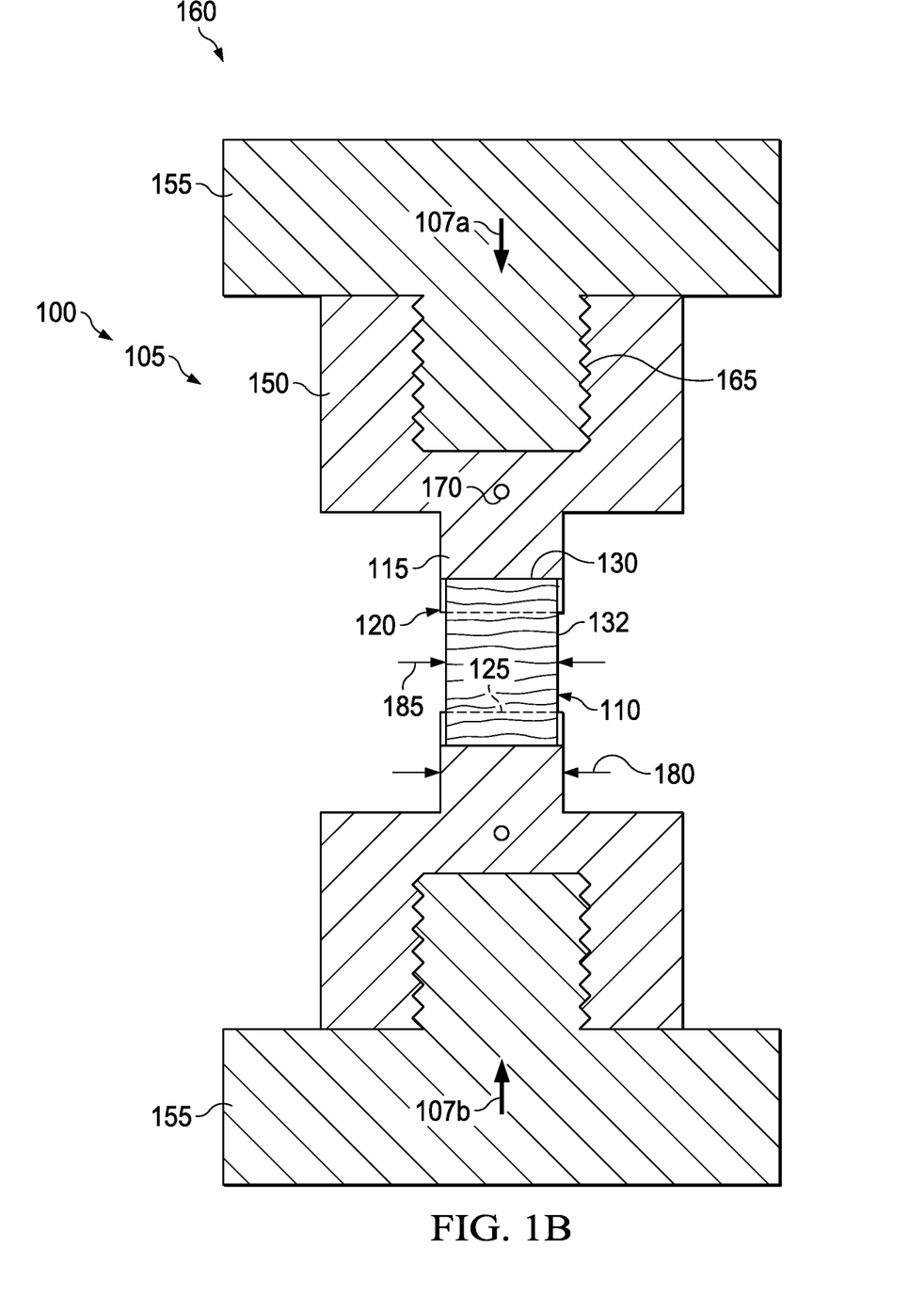
FIG. 1B presents a cross-sectional side view of the example apparatus shown in FIG. 1A.
Figure 1C:
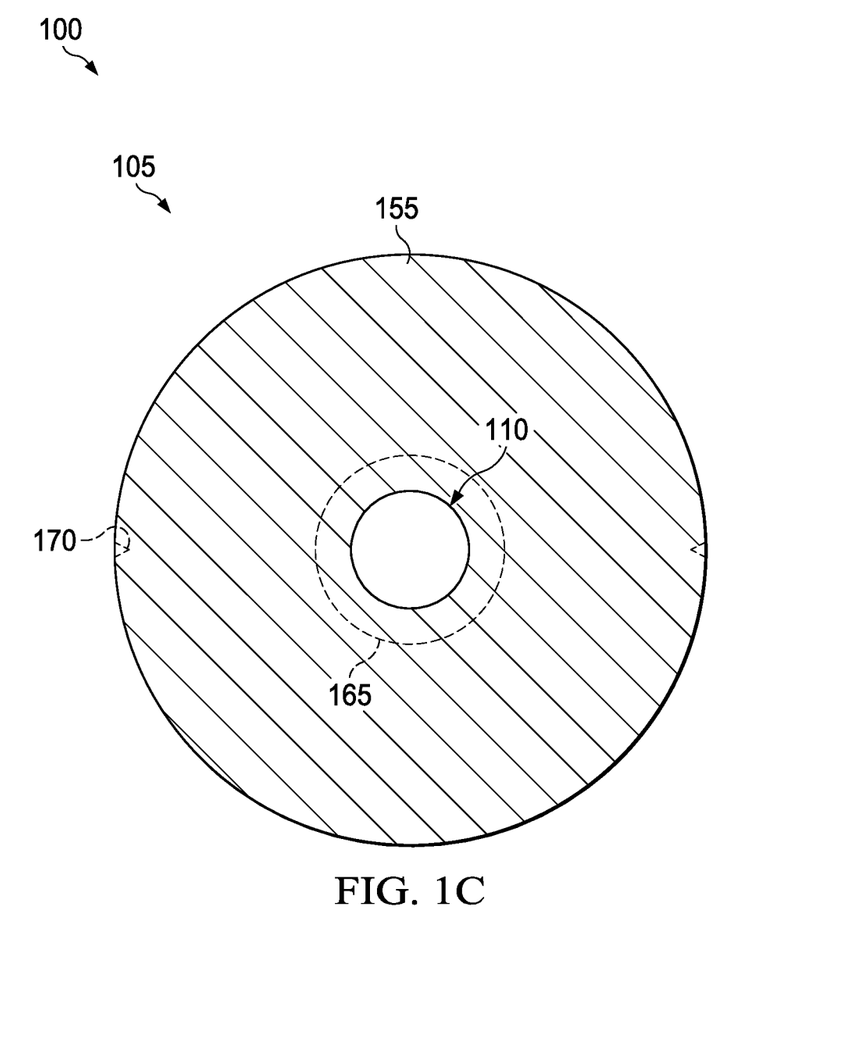
FIG. 1C presents a cross-sectional bottom view of the example apparatus shown in FIG. 1A.

One embodiment of the disclosure is an apparatus for measuring mechanical properties of a rock formation (e.g., e.g., shale, sandstone or other rock formations for oil and gas production as familiar to those skilled in the pertinent arts). FIGS. 1A, 1B and 1C present a cross-sectional front, side and bottom views, respectively, of an example apparatus 100 embodiment of the disclosure.

With continuing reference to FIGS. 1A-1C throughout, embodiments of the apparatus 100 can comprise force application fixtures 105 configured to apply opposing compressive forces 107a, 107b to a disc-shaped sample 110 of a core plug specimen from the rock formation. Non-limiting examples of types of core plug specimens include rotary sidewall, regular, whole, outcrop or other core plugs familiar to those skilled in the pertinent arts. Each of the force application fixtures 105 can include an applicant portion 115 having an end cap 120. The end cap 120 can have a shaped surface 125 that is configured to conform with a portion 130 of a non-planar side 132 of the disc-shaped sample 110 such that substantially an entire volume of the disc-shaped sample (e.g., at least about 90 percent of the total volume, and in some embodiments at least about 99 percent of the total volume) experiences a compressive stress when the opposing compressive forces 107a, 107b are applied to the portions 130 of the non-planar side 132 of the sample 110.

Embodiments of the disc-shaped sample 110 can be substantially cylindrically shaped, e.g., a shape substantially corresponding to the shape of a core plug specimen from which the sample is derived from. For instance, some embodiment of the disc-shaped sample 110 can have a cylindrical shape, e.g., as defined by planar base ends 135 having substantially circular shaped perimeters where the diameter 140 of the base ends do not vary by more than about ±20 percent, and in some embodiments, not more than about ±10 percent, and in some embodiments not more than about ±1 percent, around the entire circumference of the base end 135.

In some embodiments, the disc-shaped sample 110 can be further processed to have one or more flat faces on the side 132, but, still retain a substantially cylindrically shape, with the base ends 135 having the substantially circular shaped perimeters. As a non-limiting example, the sample 110 can be processed by further cutting or grinding such that the base ends 135 have hexagonal, octagonal or decagonal shaped perimeters with the side 132 having 6, 8 or 12 flat faces, respectively distributed around the circumference of the base end 135.

For any embodiments of the disc-shaped samples 110, to facilitate the application of the compressive stress to the entire volume of the disc-shaped sample 110, the shape of the end cap surfaces 125 can be configured to have a shape that is a negative or inverse of the shape of the portion 130 of the non-planar side 132 of the disc-shape sample 110 so as to wrap around and conformaly contact the portion 130 of the sample's side 132.

For some embodiments, the surfaces 125 of the end caps 120 are configured to extend along the non-planar side 132 of the disc-shaped sample 110 (e.g., along the circular shaped side of a substantially cylindrically shaped sample), such that the end-to-end distance 145 of each of the end caps 120 is a value in a range from about 0.7 to about 0.9 times a diameter 140 of the disc-shaped sample 110.

In some embodiments, having an end-to-end distance 145 equal to about 0.8 times the diameter 140, represents a balance between avoiding the risk of the end caps 120 touching and damaging each other during stress testing versus avoiding the introduction of non-compressive stresses during testing. For instance, for some end cap designs where the end-to-end distance 145 is less than about 0.7 times the diameter 140 the application of the opposing compressive forces 107, 107b, may undesirably produce a mixed-mode of mechanical failure comprising both compressive and shear stresses. For instance, for some end cap designs where the end-to-end distance 145 is greater than about 0.9 times the diameter 140 the application of the opposing compressive forces 107, 107b, may undesirably result in the two end caps 120 contacting each other during the mechanical failure testing of the sample, resulting in damage to the end cap 120 or other parts of the apparatus 100.

As illustrated in FIGS. 1A-1C, embodiments of the end caps 120 of the applicant portions 115 of the force application fixtures 105 can have identically shaped surfaces 125. However, in other embodiments, the end caps 120 could have differently shaped surfaces 125, provided that the shaped surfaces 125 still conform to the portion 130 of a non-planar side 132 of the sample so that substantially the entire volume of the sample experiences the compressive stress when the opposing compressive forces 107a, 107b are applied.

As further illustrated in FIGS. 1a-1c, some embodiments of the force application fixtures 105 can each include a connection portion 150, the connection portions 150 configured to attach the force application fixtures 105 to actuators 155 of a load frame device 160. For instance, the connection portion 150 can include a threaded opening 165 to allow attachment to one of two opposing actuators 155 of a hydraulic load frame device 160. One skilled in the pertinent arts would appreciate how the connection portion 150 could be adapted to have other connection mechanisms to the actuators 155.

As also illustrated in FIGS. 1A-1C, some embodiments of the force application fixtures 105 can each include notches 170 to hold in place end pins 172, the end pins 172 being part of sensors of an extensometer device configured to measure axial displacements of the disc-shaped samples 110 during the application of the opposing compressive forces 107a, 107b. For instance, each force application fixture 105 can include two notches, e.g., on opposite sides of the fixture 105, shaped so that the end pins 172 are held in place during mechanical testing of the sample 110.

As further illustrated in FIG. 1B, some embodiments of the end caps 120 have a width 180 that is substantially equal to or greater than a thickness 185 of the disc-shaped sample 110, the width 180 being in a dimension that is perpendicular to the dimension of the end-to-end distance. In some embodiments of the end caps 120, the width 180 can be substantially equal to the thickness 185 of the disc-shaped sample 110 (e.g., equal to the thickness within about ±10 percent, or within about ±1 percent, in some embodiments). Configuring the end caps 102 to have a width 180 that is substantially equal to or greater than the sample's thickness 185 can facilitate applying the compressive stress to the entire volume of the disc-shaped sample 110. For instance, for embodiments where the end caps 102 have a width 180 that is less than the sample's thickness 185, there may be an increased risk of introducing non-compressive stresses into the sample (e.g., bending or shearing stresses) when the opposing compressive forces 107a, 107b are applied to the disc-shaped sample 110.

In some embodiments, the end-to-end distance 145 of each of the end caps 120 is a value in a range from about 1.4 to about 2.5 times (and in some embodiments, about 1.4 to about 1.8 times) the width 180 of the end caps 120, the width of the end caps being in the dimension that is perpendicular to a dimension of the end-to-end distance 145. Having the end-to-end distance 145 equal to about 1.4 to about 1.8 times the width 180 of the end caps 120 can facilitate applying the compressive stress to the entire volume of the disc-shaped sample 110, e.g., when the sample 110 has a diameter 140 to thickness 185 ratio of about 2:1.

For instance, consider samples 110 having thicknesses 185 of 0.5, 1 or 2 inches and diameters of 1, 2 or 4 inches, respectively. The width 180 of the end caps 120 can be configured to have a width 180 of at least about 0.5, 1 or 2 inches, respectively, and the surface 125 of end caps 120 can be configured such that the end-to-end distance 145 equals a value in the range from about 1.4 to about 2.5 times the width 180 (e.g., end-to-end distances 145 ranging from about 0.7 to 1.25 inches, 1.4 to 2.5 inches or 2.8 to 5.0 inches, respectively for widths 180 of 0.5, 1 or 2 inches, respectively).

Based upon the present disclosure, one skilled in the pertinent arts would appreciate how the end-to-end distance 145 and the width 180 of the end caps 120 could be adjusted depending upon the particular size and shape of the sample 110 to be tested, e.g., so as to ensure that substantially an entire volume of the disc-shaped sample experiences a compressive stress during the application of the opposing compressive forces 107a, 107b. For example, if a cylindrically shaped sample 110 has a diameter 140 to thickness 185 ratio of about 4:1 or 1:1 then the end-to-end distance 145 and/or width 180 of the end caps 120 may be adjusted, e.g., as guided by simulations and experiments such further disclosed below, to ensure that substantially the whole volume of such samples 110 experience the compressive stress.

Figure 2:
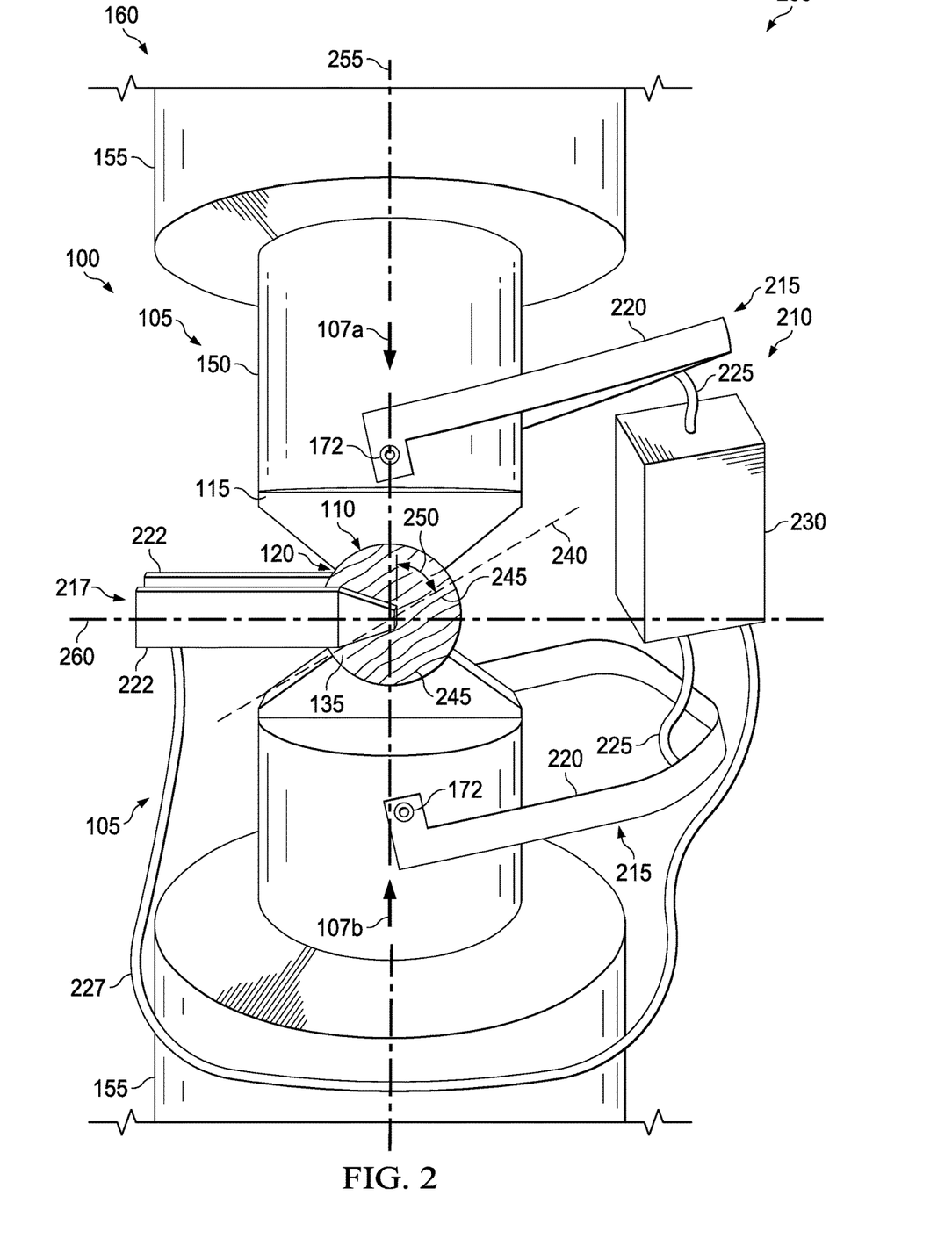
FIG. 2 presents a perspective view sketch of an example system embodiment of the disclosure.
Figure 2A:
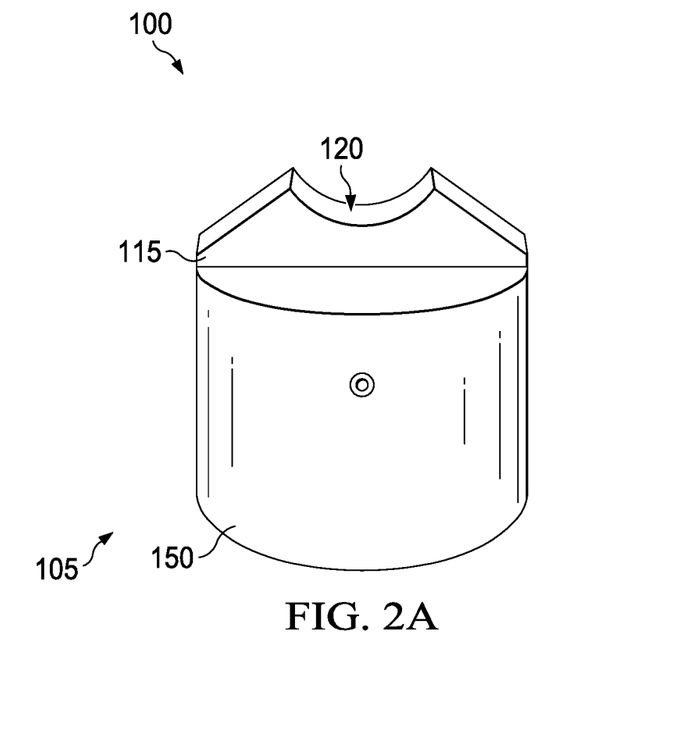
FIG. 2A presents a perspective view sketch of an application fixture prior to placing the disc-shaped sample in the applicant portion to contact the shaped surface of the end cap of the application fixture.

Another embodiment of the disclosure is a system for measuring mechanical properties of a rock formation. FIG. 2 presents a perspective view of a sketch of an example embodiment of the system 200 of the disclosure. FIG. 2A presents a perspective view sketch of an application fixture 105 prior to placing the disc-shaped sample 110 in the applicant portion 115 to contact the shaped surface 125 of the end cap 120 of the application fixture 105. The system 200 can include any of the embodiments of the apparatus 100 discussed in the context of FIGS. 1A-1C.

With continuing reference to FIGS. 1A-2A throughout, the system 200 can include the force application fixtures 105 (e.g., two opposing fixtures) of the apparatus 100, a load frame device 160, and an extensometer device 210.

The load frame device 160 can include actuators 155 (e.g., two opposing actuators) configured to apply opposing compressive forces 107a, 107b to a disc-shaped sample 110 of a core plug specimen.

The extensometer device 210 can include sensors 215, 217 (e.g., linear variable differential transformer sensors) to measure axial and lateral displacements (e.g., typically in in vertical and horizontal directions, respectively, when the device is oriented as shown in FIG. 2) of the disc-shaped sample when the opposing compressive forces 107a, 107b are applied to the disc-shaped sample. For instance, some embodiments of sensors 215 can include end pins 172 configured to be coupled to the force application fixtures (e.g., physically resting inside of notches 170 in the side of the connection portion 150 of the fixture 105). The end pins 172 can be connected to arms 220 of the axial displacement sensor 215, the arms 220 configured to record axial displacements of the sample 110 during compression stress testing. For instance, some embodiments of lateral displacement sensor 217 include one or more sensor arms 222 (e.g., a pair of arms 222 coupled to opposite base ends of the sample) configured to hold the base ends 135 of the disc-shaped sample 110 the lateral displacement sensors arms 222 are configured to measure the lateral displacement of the disc-shaped sample 110 when the opposing compressive forces 107a, 107b are applied. For instance, when the disc-shaped sample 110 has a thickness 185 of about 0.5 inches, then the lateral displacement sensor arms 222 can be configured to hold an about 0.5 inch thick sample. One skilled in the pertinent art would understand how the axial and lateral displacements of the disc-shaped sample 110 could be recorded by the sensors 215, 217 in the form of voltages, which are then transmitted (e.g., via data transmission lines 225, 227) to a recording and control module 230 of the extensometer device 210 for data processing.

As discussed above in the context of FIGS. 1A-1C, the force application fixtures 105 are couplable to the actuators 155, e.g., through a connection portion 150 of the fixture. As also discussed in the context of FIGS. 1a-1c, in some embodiments, each of the force application fixtures 105 includes an applicant portion 115, having an end cap 120. The end cap 120 has a shaped surface (e.g., surface 125) that is configured to conform with a portion 130 of a non-planar side 132 of the disc-shaped sample 110 such that substantially an entire volume of the disc-shaped sample experiences a compressive stress when the opposing compressive forces 107a, 107b are applied to the portions of the non-planar side 132.

Figure 3:
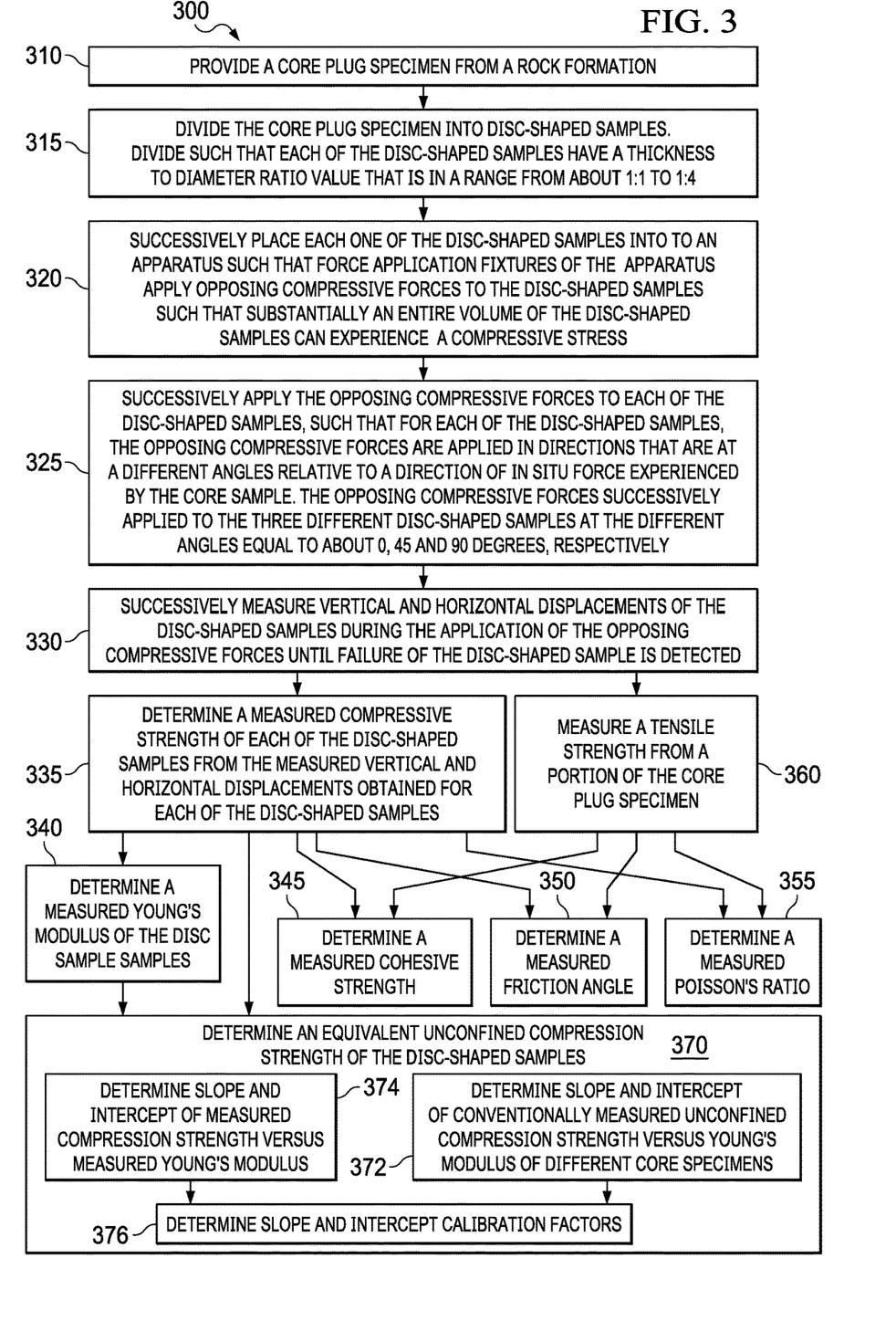
FIG. 3 presents a flow diagram of selected steps of an example method embodiment of the disclosure.

Another embodiment of the disclosure is a method of measuring mechanical properties of a rock formation. FIG. 3 presents a flow diagram of selected steps of an example method 300 of the disclosure. The method 300 can be implemented by any of the embodiments of the apparatus 100 and the system 200 such as disclosed in the context of FIGS. 1A-2.

With continuing reference to FIGS. 1-3 throughout, the embodiments of the method 300 can include providing a core plug specimen from the rock formation (step 310). One skilled in the pertinent art would be familiar with the operation of conventional coring tools, such as rotary coring tools, to obtain such a specimen. For instance, in some embodiments, providing the core plug specimen from the rock formation can include using downhole core drilling equipment to cut a cylindrically-shaped core plug specimen from axially diagonally or laterally oriented side wall portions of a well bore and catching and storage equipment to capture and transport the core plug sample to the surface for mechanical testing as disclosed herein.

Embodiments of the method 300 can also include dividing the core plug specimen into disc-shaped samples (step 315). One skilled in the pertinent art would be familiar with the operation of conventional cutting or grinding tools to divide the specimen into, e.g., same-dimensioned disc-shaped samples 110. For instance, in some embodiments, the dividing of the core plug specimen into same-dimensioned disc-shaped samples, as part of step 315, can include separating the specimen into the disc-shaped samples such that each of the disc-shaped samples have a thickness to diameter ratio value that is in a range from about 1:1 to 1:4, and in some embodiments, about 1:2. For instance, in some embodiments, core plug specimen having a diameter of about 1 to 2 inches (2.5 to 5 cm) and length of about 1 to 4 inches (2.5 to 10 cm) can be cut into multiple 0.5 inch or 1 inch thick disc-shaped samples and the end faces of each of the sample can be grinded to obtain the desired thickness to diameter ratio.

Embodiments of the method 300 can further include successively placing each one of the disc-shaped samples into to an apparatus (step 320), e.g., one sample 110 at a time into apparatus 100, such that force application fixtures 105 of the apparatus can apply opposing compressive forces 107a, 107b to the disc-shaped samples 110 such that substantially an entire volume of the disc-shaped samples 110 is configured to experience a compressive stress.

Embodiments of the method 300 can further include successively applying the opposing compressive forces to each of the disc-shaped samples 110 (step 325). For each of the disc-shaped samples 110, the opposing compressive forces 107a, 107b are applied in directions that are at different angles relative to a direction of in situ force experienced by the core plug specimen. For instance, the direction of in situ force experienced by the core plug specimen can be substantially perpendicular to the average plane of the substantially parallel laminated layers (e.g., average plane 240 of the layers 245, FIG. 2) of the disc-shaped samples 110 and therefore each of different the samples 110 can be rotated such that directions of the opposing compressive forces 107a, 107b are applied at different angles (e.g., angle 250, FIG. 2) relative to the average plane 240 of the laminated layers 245 of the samples 110.

For example, in some embodiments, the opposing compressive forces 107a, 107b can be successively applied, as part of step 325, to three different disc-shaped samples 110 at different angles 250 equal to about 0, 45 and 90 degrees, respectively. However, in other embodiments, additional samples 110 could be compression tested at different angles (e.g., intermediate angles of 22.5 and 67.5 degrees, respectively), to provide more detailed information about anisotropy of the mechanical properties present in the specimen from which the samples 110 are derived.

Embodiments of the method 300 can further include successively measuring axial and lateral displacements of the disc shaped samples during the application of the opposing compressive forces until failure of the disc-shaped sample is detected (step 330). The axial displacement can be measured along a first axis (e.g., axial axis 255, FIG. 2), the first axis being parallel to the directions of the opposing compressive forces 107a, 107b. The lateral displacement can be measured along a second axis (e.g., lateral axis 260, FIG. 2), the second axis being perpendicular to the directions of the opposing compressive forces 107a, 107b.

Some embodiments of the method 300 can further include determining a measured compressive strength of each of the disc shaped samples from the measured axial and lateral displacements obtained for each of the disc shaped samples (step 335). One skilled in the pertinent arts would be familiar with the equations used to determine compressive strength from such displacement measurements. For example determinations of unconfined compressive strength can be performed by compression of cylindrical spacemen and detecting force of its mechanical failure with resulted permanent deformation.

Some embodiments of the method 300 can further include determining a measured Young's Modulus for each of the disc shaped samples (step 340) using the measured compressive strength of each of the disc shaped samples (e.g., measured in step 335). One skilled in the pertinent arts would be familiar with the equations (e.g., E=σ/ε, where σ is compressional stress and ε is axial strain) used to determine Young's Modulus from such measured compressive strength values.

Some embodiments of the method 300 can further include determining a measured cohesive strength (step 345), a measured friction angle (step 350), or a measured Poisson's ratio (step 355) of each of the disc shaped samples, using the measured compressive strength (e.g., determined in step 335) of each of the disc shaped samples and a tensile strength measured for a portion of the core plug specimen (step 360). One skilled in the pertinent arts would be familiar with how to determine tensile strength from core plug specimens, e.g., using ASTM standard D3967. For example a disc shape specimen can be compressed from two opposed non planar sides, using force applicators that are substantially flat or slightly curved to assure minimum area of contact between applicators and the specimen. The diameter to thickness ratio is typically in a range about 2 to 2.5. The compressive force is continuously increased until failure of the specimen. The Tensile strength ($\sigma_t$) can be calculated by formula:

$$\sigma_t = 2F/(\pi dL)$$

where, F equals the compressive force at failure, d equals the specimen's diameter and L equals the specimen's thickness.

One skilled in the pertinent arts would be familiar with how to determine Poisson's ratio from such compressive strength and tensile strength measurements. For example Poisson's ratio (v) can be determined from the equation:

$$v = -\varepsilon_z/\varepsilon_x,$$

where $\varepsilon_z$ equals axial strain during compression and $\varepsilon_x$ equals strain in the direction perpendicular to the direction of compression.

One skilled in the pertinent arts would be familiar with how to determine Cohesive strength and Friction angle can be also determined using Mohr-Coulomb failure envelope. ASTM D7012, Standard Test Methods for Compressive Strength and Elastic Moduli of Intact Rock Core Specimens under Varying States of Stress and Temperatures.

Some embodiments of the method 300 can further include determining an equivalent unconfined compression strength of the disc shaped samples (step 370). Determining the equivalent unconfined compression strength in accordance with step 370 can include determining a conventional slope and conventional intercept from plots of conventionally determined unconfined compression strength versus conventionally determined Young's Modulus (step 372), e.g., by linear regression analysis. The unconfined compression strength and the conventionally determined Young's Modulus can be determined from one or more different core specimens obtained from the rock formation, or, in some embodiments from other rock formation including other types of rock formations than the rock formation from which the core plug specimen was obtained. One skilled in the pertinent arts would be familiar with how to determine the unconfined compression strength conventionally determined Young's Modulus. For example Young's modulus (E) can be determined using equation:

$$E = C_1\sigma/\varepsilon,$$

where $C_1$ equals a predetermined correlation coefficient, σ equals compressional stress, and equals axial strain. The compressive strength $\sigma_c$ equals $C_2\sigma_f$, where $C_2$ is another predetermined correlation coefficient and $\sigma_f$ equals measured stress at failure.

Determining the equivalent unconfined compression strength (step 370) can include determining a measured slope and measured intercept (step 374) from plots of the measured compressive strength (e.g., as determined in step 335) versus a measured Young's Modulus (e.g., as determined in step 340) for at least one of the disc shaped samples 110, e.g., by linear regression analysis.

Determining the equivalent unconfined compression strength (step 370) can include determining a slope calibration factor (step 376) (e.g., as ratios of the measured slope to the conventional slope) and an intercept calibration factor (e.g., as ratios of the measured intercept to the conventional intercept).

The slope calibration factor and the intercept calibration factor can then be used to convert the measured compressive strength to the equivalent unconfined compression strength in accordance with step 370.

Based on the present disclosure one skilled in the pertinent arts would understand how analogous steps could be performed to determine an equivalent unconfined cohesive strength, friction angle, or Poisson's ratio for each of the samples 110.

EXPERIMENTS

To further illustrate various features of the disclosure, an example embodiment of the apparatus of the disclosure and the example apparatus's use for measuring the mechanical properties of rock formation sample using embodiments of the system and method of the disclosure, are presented below.

Figure 4:
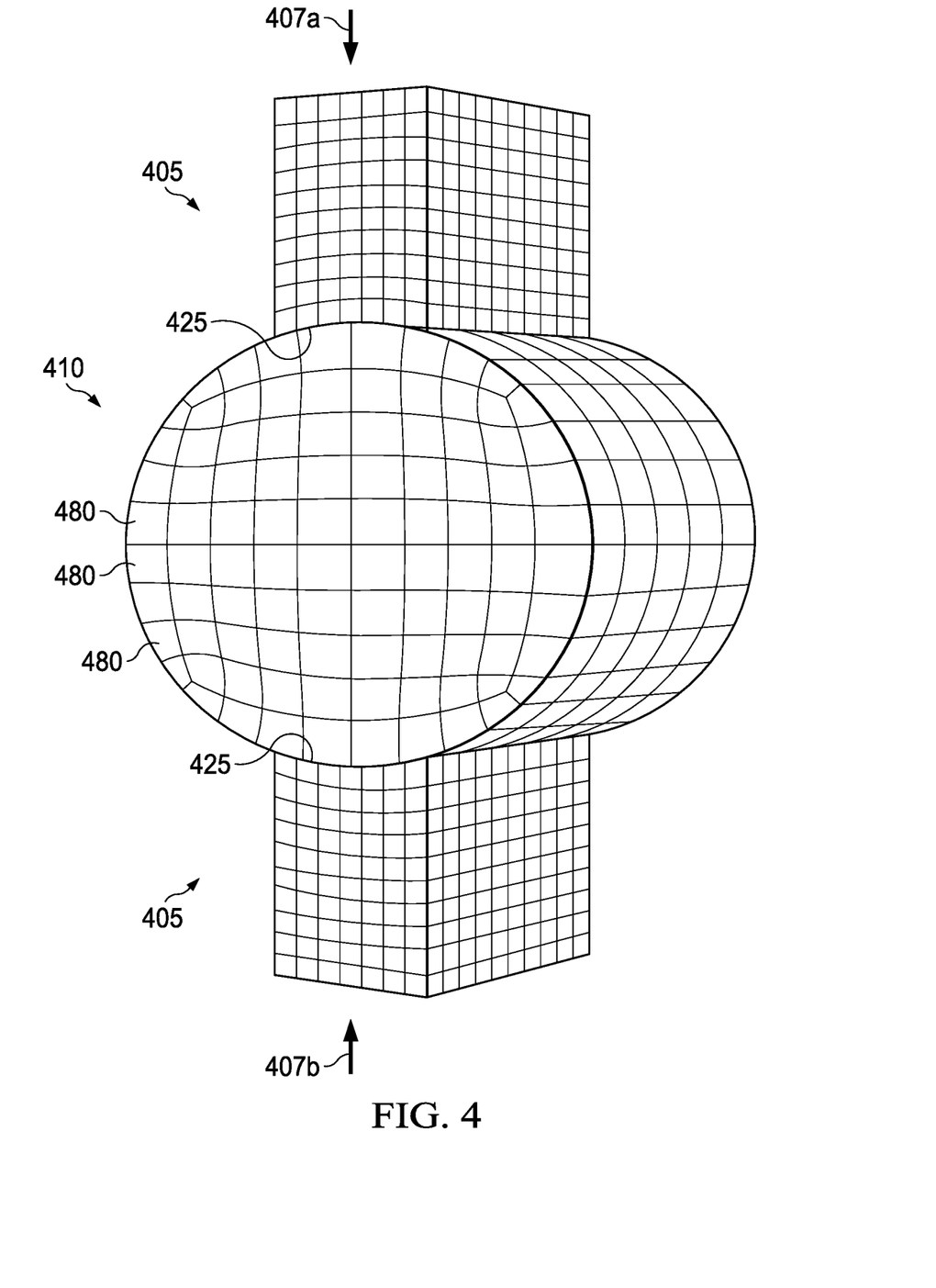
FIG. 4 presents a perspective view of an example design of simulated force application fixtures to apply compressive stress to a simulated disc-shaped sample in accordance to the principles of the disclosure.

Experiment 1: Simulation Experiments to Develop an Example Embodiment of the Apparatus Computer simulation software (Abaqus FEA, Dassault Systémes Waltham, Mass.) was used to develop and test the ability of various model embodiments of the apparatus for their ability to created compression stress concentration for simulated cylindrically-shaped object, e.g., having a diameter to thickness ratio of 2:1 for some simulations. Simulated forces (e.g., from about 0 to 1E+7 Newtons) for various end cap shaped surface designs were evaluated for simulated displacement distributions and stress concentrations inside of a simulated object 410 to evaluate the end cap ability to produce compressive forces throughout defined volume elements 480 of the simulated object.

FIG. 4 presents a perspective view of an example simulated object 410 and example simulated end cap surfaces 424 of simulated force application fixtures 405 used to evaluate the distribution of compressive forces in a simulated object 410 in accordance to the principles of the disclosure. The object 405 was represented by about 500 volume elements 480 each of about 1 mm$^3$ in volume).

Figure 5:
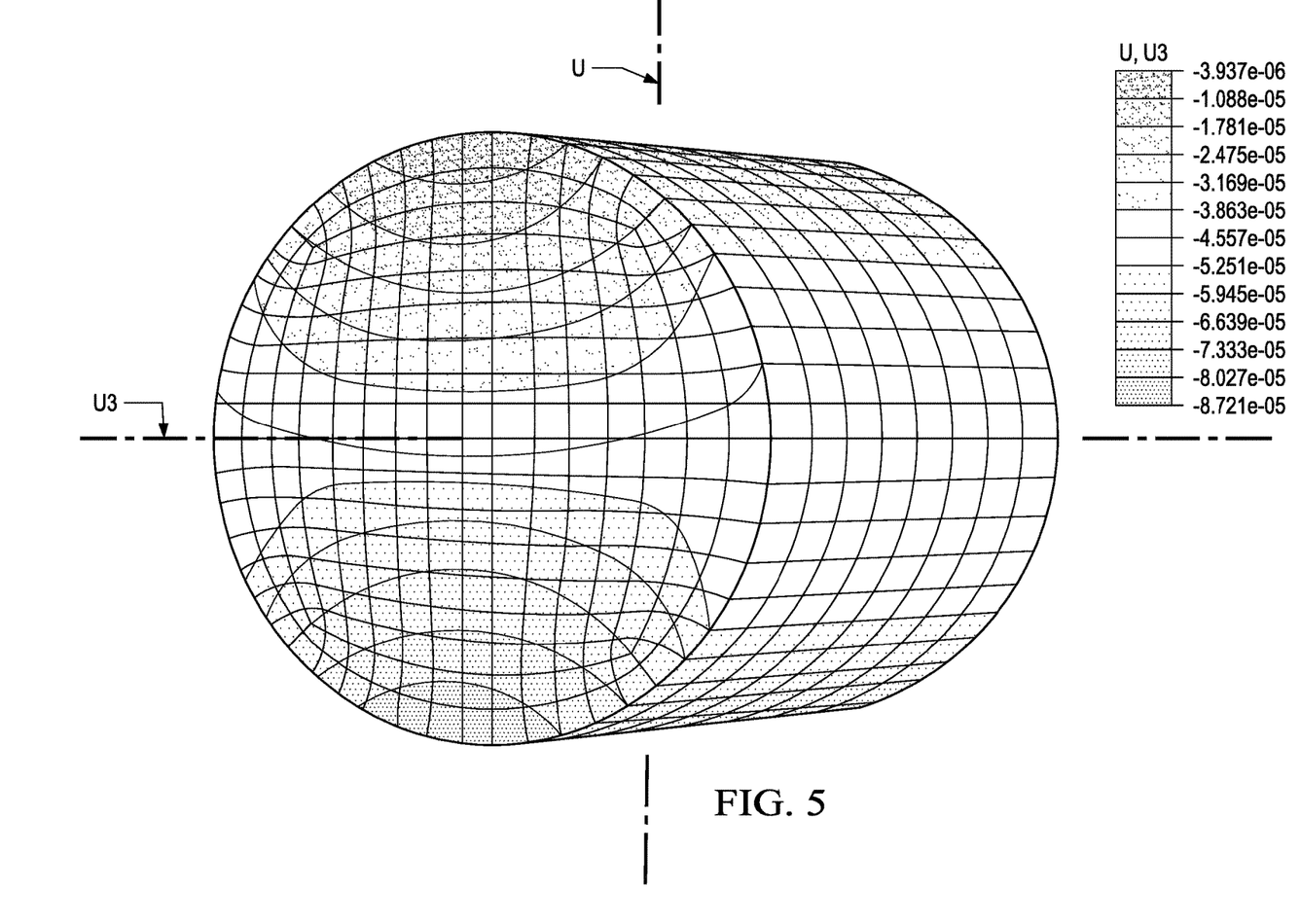
FIG. 5 presents a perspective view of example simulated axial displacement distributions of a simulated disc-shaped sample subjected to a simulated compressive stresses from simulated force application fixtures in accordance to the principles of the disclosure.

FIG. 5 presents a perspective view of a simulated object 410 showing a distribution plot of the numerical simulation results of calculated axial displacements for each of the simulated volume elements 480 (FIG. 4) in axial dimension U and lateral dimension U3. The calculated axial displacement distribution of the elements 480 representing in the simulated object 410 are the result of a simulated application of opposing compressive forces 407A 407B in the axial dimension through simulated force application fixtures 404 such as presented in FIG. 4.

Based upon the present disclosure, one skilled in the pertinent arts would appreciate how analogous simulations could be conducted to develop end cap shapes appropriate for disc samples cut to have different shapes e.g., different thicknesses different diameters or top and bottom end faces with non-circular perimeters (hexagonal, octagonal or other shapes whose perimeters may have one or more planar portions).

Experiment 2: Evaluation of Prototype Force Application Fixtures

Prototype example force application fixtures were machined and experiments were performed to examine the correlation between mechanical properties of disc-shaped samples and data recorded using the prototype fixtures. A pair of prototype force application fixtures were machined to have shapes similar to the fixtures described in the context of FIGS. 1A-2 for the testing of disc-shaped samples as described below. The end cap of the prototype force application fixtures was machined to have a shaped surface (e.g., surface 125 FIG. 1A) conforming with a portion of a non-planar side of the disc-shaped samples such that the end-to-end distance of the end caps equaled 1.6 inches. A connection portion of the prototype force application fixtures was machined to include threaded openings so that the fixture could be attached to actuators of a hydraulically powered load frame device (Model Landmark®, MTS Systems Corporation, Minnesota). Notches were machined into sides of the prototype force application fixtures so that end pins of sensors of the extensometer device could be attached thereto to measure axial displacements of the disc shaped samples during the application of the opposing compressive forces. The axial and lateral displacements of the samples were measured using linear variable differential transformer sensors of an extensometer device (Model 632.90 MTS Systems Corporation, Minnesota).

Samples for use in with the prototype force application fixtures were formed by cutting core plug specimens obtained from different types of formations (e.g., specimen A for a shale formation, specimen B for a sand stone formation). The samples were trimmed as needed to form uniform sized disc-shape having a diameter of 2.0 inches (e.g., about 5 cm) and width of 0.50 inches (e.g., about 1.3 cm). The samples were then placed in between the prototype force application fixtures such that the end caps of the fixtures contacted the sides of the disc sample, and then the disc-shaped samples were subjected to compression until failure, e.g., opposing compressive forces ranging from about 2000 to about 14000 psi (about 13800 kPa to about 96500 kPa).

Figure 6:
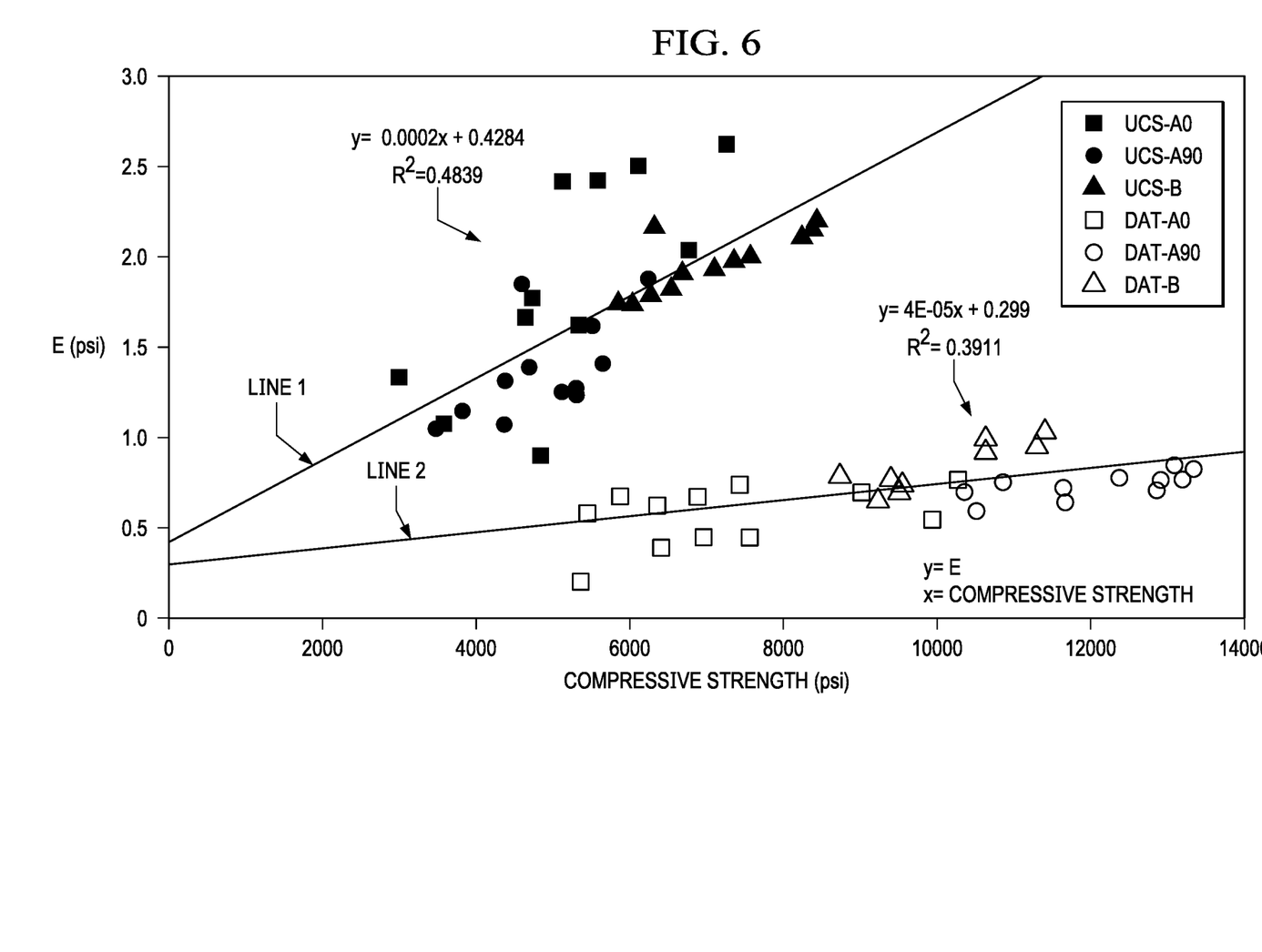
FIG. 6 presents a plot of Young's modulus (E) versus compressive strength for disc-shaped samples of rock formations tested using a conventional system and method (squares), and tested using a prototype apparatus, system and method of the disclosure (triangles).

FIG. 6 presents plots of the Young's modulus (E) versus the compressive strength for disc-shaped samples of the rock formations specimens measured using the prototype force application fixtures, system and method (triangles), and, plots of conventionally measured Youngs modulus versus a conventional unconfined compressive strength (UCS) measured using a conventional apparatus and methods (squares). The conventional UCS measurements were conducted according to ATSM D7012 using the same load frame device but with conventional application fixtures.

For the specimens obtained from shale rock formations, UCS measures were conducted on two different core samples oriented at 0 or at 90 degree angles (e.g., angle 250 FIG. 2) relative to the average plane of the substantially parallel laminated layers visible in such type A specimens (e.g., UCS-A0 and UCS-A90, respectively). Compressive strength measurements of the disc-shaped samples obtained from a same core sample, measured in accordance with the disclosure, were conducted with two different ones of the disc shaped samples oriented at 0 or 90 degrees relative to the average plane of the substantially parallel laminated layers visible in type B specimens (e.g., DAT-A0 and DAT-A90, respectively). For the specimens obtained from sand stone rock formations, due to the homogeneity of the specimens (e.g., no visible layers present) the UCS measurements of core samples (e.g., UCS-B) and the compressive strength measurements of the disc-shaped samples obtained from a sample core sample, measured in accordance with the disclosure, (e.g., DAT-B) were conducted with no particular orientation of the samples found to be important.

FIG. 6 also presents a linear regression analysis best-fit line (Line 1) of the combined UCS measurements obtained for the samples obtained from the shale and sand stone rock formations (squares) and a linear regression analysis best-fit line (Line 2) of the combined measurements obtained for the samples obtained from the shale and sand stone rock formations, measured in accordance with the disclosure. As illustrated regardless of the type of sample (e.g., sandstone or shale rock formations) the UCS measures follow a substantially same relationship of Young's modulus versus compression strength that can be modeled by line 1. Likewise the measured Young's modulus and measured compressive strength measurements of the disc-shaped samples regardless of the type of sample, measured in accordance with the disclosure, followed a substantially same relationship of Young's modulus versus compression strength that can be modeled by line 2.

As part of the present disclosure we recognized that the difference in the slope and intercept of line 1 and line 2 can be used to determine a slope calibration factor and an intercept calibration factor to convert the measured compressive strength, measured in accordance with the disclosure, into an equivalent UCS measurement measured using conventional procedures with conventional core samples. Moreover because different types of rock formations (e.g., sandstone and shale) followed substantially the same regression line, we expect that it may be possible, to just obtain such calibration factors just one time and then apply the resulting correlation factor generally to other specimens to determine equivalent UCS measurement, subject to the particular shape of sample.

Because the disc shape samples are all obtained from a same core specimen, we found that the variance in the measured compressive strength can be substantially smaller than, e.g., the results from conventional measurements made on different core specimens obtained from different locations in the rock formation. For instance, consider a shale formation where different core specimens obtained from locations that are only 10 inches apart from each other, and can have UCS values that vary by 30% or more, e.g., due to the different clay contents of the core specimens. The resulting average UCS from such different core specimens will have a variance of about ±30%. In contrast, the average measured compressive strength obtained from multiple disc shaped samples, divided from the same core specimen in accordance with the present disclosure, can have a variance of other a few percent. Moreover because the disc samples can be tested at different angles a fuller picture of the anisotropy in mechanical properties of the specimen can be obtained.

Consequently, it is possible to obtain more precise measurements for the core specimens than possible from conventional measurements made using two or more different core sample which of course will have to be from at least somewhat different locations of the rock formation. In turn, having more precise measurements allows more precise assessments of well-bore stability such as, better understands the ability of wellbores to tolerate stresses on the wellbore during various production stages of oil and gas extraction or better estimating how much fluid can be pumped into the wellbore and the weight of drilling mud can be used.

Additionally, we recognized, as part of the present disclosure, that relationships between conventionally measured tensile strength, cohesive strength, friction angle, or Poisson's ratio versus these properties, measured in accordance with the disclosure, could be determined and plotted similar to that presented in FIG. 6 and a regression analysis of these relationships could be performed to determine calibration factors for these material properties, analogous to that presented above.

Those skilled in the art to which this application relates will appreciate that other and further additions, deletions, substitutions and modifications may be made to the described embodiments.

What is claimed is:

1. An apparatus for measuring mechanical properties of a rock formation, the apparatus comprising:
   force application fixtures configured to apply opposing compressive forces to a disc-shaped sample of a core plug specimen from the rock formation, wherein each of the force application fixtures include an applicant portion having an end cap, the end cap having a shaped surface that is configured to conform with a portion of a non-planar side of the disc-shaped sample such that substantially an entire volume of the disc-shaped sample experiences a compressive stress when the opposing compressive forces are applied to the portions of the non-planar side, wherein the force application fixtures includes notches to hold in place end pins, the end pins part of an extensometer device to measure axial displacements of the disc shaped samples during the application of the opposing compressive forces.

2. The apparatus of claim 1, wherein the surface of the end cap is configured to extend along the non-planar side of the disc-shaped sample configured as the side of the disc-shaped sample substantially shaped as a cylinder, such that the end-to-end distance of each of the end cap is equal to a value in a range from about 0.7 to about 0.9 times a diameter of the disc-shaped sample.

3. The apparatus of claim 1, wherein the force application fixtures include a connection portion, the connection portion configured to attach the force application fixtures to actuators of a load frame device.

4. The apparatus of claim 1, wherein a width of the end cap is substantially equal to or greater than a thickness of the disc-shaped sample, the width being in a dimension that is perpendicular to a dimension of the end-to-end distance.

5. The apparatus of claim 1, wherein an end-to-end distance the end cap is a value in a range from about 1.4 to about 1.8 times a width of the end cap, the width of the end cap being in a dimension that is perpendicular to a dimension of the end-to-end distance.

6. A system for measuring mechanical properties of a rock formation, the system comprising:
   a load frame device, the load frame device including actuators configured to apply opposing compressive forces to a disc-shaped sample of a core plug specimen from the rock formation;
   an extensometer device, the extensometer device including sensors to measure axial and lateral displacements of the disc-shaped sample when the opposing compressive forces are applied to the disc-shaped sample; and
   force application fixtures coupled to the actuators, wherein each of the force application fixtures include an applicant portion having an end cap, the end cap having a shaped surface that is configured to conform with a portion of a non-planar side of the disc-shaped sample such that substantially an entire volume of the disc-shaped sample experiences a compressive stress when the opposing compressive forces are applied to the portions of the non-planar side.

7. The system of claim 6, wherein the sensors of the extensometer includes one or more sensors coupled to sides of the force application fixtures the sensors configured to measure the axial displacement of the disc-shaped sample when the opposing compressive forces are applied.

8. The system of claim 6, wherein the sensors of the extensometer device includes one or more sensor arms configured to hold to base ends of the disc-shaped sample the sensor arms configured to measure the lateral displacement of the disc-shaped sample when the opposing compressive forces are applied.

9. The system of claim 6, wherein the surface of the end cap is configured to extend along the non-planar side of the disc-shaped sample configured as the side of the disc-shaped sample substantially shaped as a cylinder, such that the end-to-end distance of each of the end cap is equal to a value in a range from about 0.7 to about 0.9 times a diameter of the disc-shaped sample.

10. The system of claim 6, wherein the force application fixtures include a connection portion, the connection portion configured to attach the force application fixtures to actuators of a load frame device.

11. The system of claim 6, wherein the force application fixtures includes notches to hold in place end pins, the end pins part of an extensometer device to measure axial displacements of the disc shaped samples during the application of the opposing compressive forces.

12. The system of claim 6, wherein a width of the end cap is substantially equal to or greater than a thickness of the disc-shaped sample, the width being in a dimension that is perpendicular to a dimension of the end-to-end distance.

13. The system of claim 6, wherein an end-to-end distance the end cap is a value in a range from about 1.4 to about 1.8 times a width of the end cap, the width of the end cap being in a dimension that is perpendicular to a dimension of the end-to-end distance.

14. A method of measuring mechanical properties of a rock formation, comprising:
   providing a core plug specimen from the rock formation;
   dividing the core plug specimen into disc-shaped samples;
   successively placing each one of the disc-shaped samples into to an apparatus such that force application fixtures of the apparatus can apply opposing compressive forces to the disc-shaped samples such that substantially an entire volume of the samples is configured to experience a compressive stress,
   successively applying the opposing compressive forces to each of the disc-shaped samples, wherein for each of the disc-shaped samples, the opposing compressive forces are applied in directions that are at a different angles relative to a direction of in situ force experienced by the core sample; and
   successively measuring axial and lateral displacements of each of the disc shaped samples during the application of the opposing compressive forces until failure of the each of the disc-shaped samples is detected, wherein:
      the axial displacement is measured along a first axis, the first axis parallel to the directions of the opposing compressive forces, and the lateral displacement is measured along a second axis, the second axis perpendicular to the directions of the opposing compressive forces.

15. The method of claim 14, wherein for three of the disc-shaped samples, the opposing compressive forces are successively applied to the three different disc-shaped samples at the different angles equal to about 0, 45 and 90 degrees, respectively.

16. The method of claim 14, wherein the dividing of the core plug specimen into same-dimensioned disc-shaped samples includes separating the core plug specimen into the disc-shaped samples such that each of the disc-shaped samples have a thickness to diameter ratio value that is in a range from about 1:1 to 1:4.

17. The method of claim 14, further including determining a measured compressive strength of each of the disc shaped samples from the measured axial and lateral displacements obtained for each of the disc shaped samples.

18. The method of claim 14, further including determining one or more of a measured cohesive strength, a measured friction angle, or a measured Poisson's ratio of each of the disc shaped samples, using the measured compressive strength of each of the disc shaped samples and a tensile strength measured for a portion of the core plug specimen.

19. The method of claim 14, further including determining an equivalent unconfined compression strength of the disc shaped samples, including
   determining a conventional slope and conventional intercept from plots of conventionally determined unconfined compression strength versus conventionally determined Young's Modulus, wherein the unconfined compression strength and the conventionally determined Young's Modulus are determined from one or more different core specimens obtained from the rock formation;
   determining a measured slope and measured intercept from plots of the measured compressive strength versus a measured Young's Modulus for at least one of the disc shaped samples; and
   determining a slope calibration factor and an intercept calibration factor.

* * * * *